United States Patent
Asanuma et al.

(10) Patent No.: US 8,156,787 B2
(45) Date of Patent: Apr. 17, 2012

(54) DEVICE FOR DETECTION OF SULFUR CONCENTRATION IN FUEL OR OIL

(75) Inventors: Takamitsu Asanuma, Mishima (JP);
Kohei Yoshida, Gotenba (JP); Hiromasa Nishioka, Susono (JP); Hiroshi Otsuki, Susono (JP); Yuka Nakata, Susono (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 568 days.

(21) Appl. No.: 12/377,039

(22) PCT Filed: Jun. 30, 2008

(86) PCT No.: PCT/JP2008/062246
§ 371 (c)(1),
(2), (4) Date: Feb. 10, 2009

(87) PCT Pub. No.: WO2009/008396
PCT Pub. Date: Jan. 15, 2009

(65) Prior Publication Data
US 2009/0241638 A1    Oct. 1, 2009

(30) Foreign Application Priority Data
Jul. 11, 2007    (JP) ................................. 2007-182225

(51) Int. Cl.
G01N 27/04    (2006.01)
G01N 33/22    (2006.01)
(52) U.S. Cl. .................... 73/23.33; 73/23.31; 73/23.32; 73/25.03

(58) Field of Classification Search .................. 73/23.2, 73/23.31, 23.32, 23.33, 25.01, 25.03
See application file for complete search history.

(56) References Cited

U.S. PATENT DOCUMENTS

| 4,724,008 A | 2/1988 | Bell et al. |
| 5,010,021 A | 4/1991 | Bell et al. |
| 5,087,574 A | 2/1992 | Bell et al. |

(Continued)

FOREIGN PATENT DOCUMENTS

EP    1 431 756 A1    6/2004

(Continued)

OTHER PUBLICATIONS

Extended European Search Report issued Mar. 9, 2011, in European Patent Application No. 08777922.9.

*Primary Examiner* — David Rogers
(74) *Attorney, Agent, or Firm* — Oblon, Spivak, McClelland, Maier & Neustadt, L.L.P.

(57) ABSTRACT

A metal compound (50) able to trap a sulfur component in exhaust gas is arranged in a flow path of the exhaust gas, a property of the metal compound (50) changing along with an increase of the amount of sulfur component trapped at the metal compound (50) is measured, and the cumulative value of the amount of $SO_X$ actually contained in the exhaust gas is calculated from the measured property. On the other hand, the assumed cumulative value of the amount of $SO_X$, assumed to be contained in the exhaust gas when assuming that fuel or oil of a sulfur concentration assumed in advance is used, is calculated. It is judged if fuel or oil with a high sulfur concentration is being used from the actual cumulative value of the amount of $SO_X$ and the assumed cumulative value of the amount of $SO_X$.

21 Claims, 13 Drawing Sheets

U.S. PATENT DOCUMENTS

| | | | |
|---|---|---|---|
| 5,134,080 A | 7/1992 | Bell et al. | |
| 5,473,890 A * | 12/1995 | Takeshima et al. | 60/285 |
| 6,200,445 B1 * | 3/2001 | Yokota et al. | 204/424 |
| 6,341,487 B1 * | 1/2002 | Takahashi et al. | 60/286 |
| 6,997,347 B2 * | 2/2006 | Peng et al. | 222/3 |
| 7,562,522 B2 * | 7/2009 | Yan | 60/286 |
| 7,788,906 B2 * | 9/2010 | Dalla Betta et al. | 60/286 |
| 2003/0041592 A1 * | 3/2003 | Nishioka et al. | 60/277 |
| 2003/0155239 A1 * | 8/2003 | Stahl et al. | 204/424 |
| 2004/0026268 A1 * | 2/2004 | Maki et al. | 205/784 |
| 2004/0040287 A1 * | 3/2004 | Beutel et al. | 60/285 |
| 2004/0063215 A1 | 4/2004 | Horiuchi et al. | |
| 2004/0198595 A1 * | 10/2004 | Chen | 502/328 |
| 2004/0209770 A1 * | 10/2004 | Nakatsuji | 502/302 |
| 2004/0261401 A1 * | 12/2004 | Ohkl et al. | 60/285 |
| 2005/0049143 A1 * | 3/2005 | Eguchi et al. | 502/330 |
| 2005/0170954 A1 * | 8/2005 | Yoshida et al. | 502/325 |
| 2006/0005532 A1 * | 1/2006 | Kitahara | 60/285 |
| 2006/0123768 A1 * | 6/2006 | Miura | 60/277 |
| 2006/0230749 A1 * | 10/2006 | Asanuma | 60/295 |
| 2006/0258014 A1 | 11/2006 | Ceccarini et al. | |
| 2007/0065341 A1 * | 3/2007 | Asanuma | 422/62 |
| 2007/0089405 A1 * | 4/2007 | Asanuma | 60/295 |
| 2008/0072575 A1 * | 3/2008 | Yan | 60/284 |
| 2008/0223020 A1 * | 9/2008 | Yoshida et al. | 60/286 |
| 2008/0245057 A1 * | 10/2008 | Odendall | 60/276 |
| 2008/0302090 A1 * | 12/2008 | Yoshida et al. | 60/286 |
| 2009/0031705 A1 * | 2/2009 | Yoshida et al. | 60/278 |
| 2009/0031709 A1 * | 2/2009 | Yoshida et al. | 60/286 |
| 2009/0038291 A1 * | 2/2009 | Yoshida et al. | 60/286 |
| 2009/0145113 A1 * | 6/2009 | Yoshida et al. | 60/285 |
| 2009/0151331 A1 * | 6/2009 | Tsujimoto et al. | 60/286 |
| 2009/0188238 A1 * | 7/2009 | Yoshida et al. | 60/285 |
| 2009/0249767 A1 * | 10/2009 | Yoshida et al. | 60/286 |
| 2009/0255233 A1 * | 10/2009 | Yoshida et al. | 60/286 |
| 2009/0308053 A1 * | 12/2009 | Nishioka et al. | 60/276 |
| 2010/0082222 A1 * | 4/2010 | Alark et al. | 701/103 |
| 2010/0089040 A1 * | 4/2010 | Handa | 60/287 |

FOREIGN PATENT DOCUMENTS

| | | |
|---|---|---|
| JP | 2 122250 | 5/1990 |
| JP | 05296970 A * | 11/1993 |
| JP | 2000-320323 | 11/2000 |
| JP | 2004 239706 | 8/2004 |
| JP | 2008 64492 | 3/2008 |
| WO | 03 029801 | 4/2003 |

* cited by examiner (A)

(B)

(C)

(D)

(A)

(B)

(C)

(A)

(B)

(A)

(B)

DEVICE FOR DETECTION OF SULFUR CONCENTRATION IN FUEL OR OIL

TECHNICAL FIELD

The present invention relates to a device for detection of sulfur in fuel or oil.

BACKGROUND ART

In the past, there have been known $SO_X$ concentration sensors for detecting the $SO_X$ concentration in the exhaust gas. These known $SO_X$ concentration sensors normally use solid electrolytes and measure the electromotive force generated by the change of $SO_X$ into sulfate ions to detect the $SO_X$ concentration in the exhaust gas (for example, see Japanese Patent Publication (A) No. 2004-239706). In this regard, if the concentration of sulfur in the fuel or oil changes, the concentration of $SO_X$ in the exhaust gas changes along with this. Therefore, if using the above $SO_X$ concentration sensor to detect the $SO_X$ concentration in the exhaust gas, it becomes possible to detect the concentration of sulfur in the fuel or oil.

However, a conventional $SO_X$ detection system using this kind of $SO_X$ concentration sensor can only operate under high temperatures and becomes bulky as an apparatus. In particular, when the $SO_X$ concentration is low, there is the large problem of not being able to detect the $SO_X$ concentration. Conventionally, as in this $SO_X$ concentration sensor, attention has only been directed at instantaneously detecting the $SO_X$ concentration. So long as trying to instantaneously detect the $SO_X$ concentration in such a way, various problems inevitably occur like as explained above.

Therefore, the inventors changed their way of thinking and focused not on instantaneously detecting the $SO_X$ concentration, but on detecting the cumulative amount of sulfur $SO_X$ released over a long period. Further, by changing their thinking in this way, it became possible to easily detect the cumulative amount of the $SO_X$ exhausted over a long period of time, rather the amount of $SO_X$ in the exhaust gas, and therefore possible to easily detect the concentration of sulfur in the fuel or oil.

DISCLOSURE OF THE INVENTION

An object of the present invention is to provide a sulfur concentration detection device able to easily detect the sulfur concentration in fuel or oil.

According to the present invention, there is provided a device for detection of the concentration of sulfur in fuel or oil, wherein a metal or metal compound able to trap a sulfur component in exhaust gas is arranged in a flow path of exhaust gas produced by combustion of fuel or oil, a property of the metal or metal compound changing along with an increase in an amount of sulfur component trapped by the metal or metal compound is measured, the amount of sulfur component trapped in the metal or metal compound is detected from a measured property, an actual cumulative value of an amount of $SO_X$ actually contained in the exhaust gas is calculated from a detected amount of sulfur component, an assumed cumulative value of an amount of $SO_X$, assumed to be included in the exhaust gas based on an operating state of the engine under the assumption that fuel or oil of a sulfur concentration assumed in advance is used, is detected, and it is judged that fuel or oil of a sulfur concentration higher than the concentration of sulfur assumed in advance is being used when the actual cumulative value of the amount of $SO_X$ becomes larger than an assumed cumulative value of the amount of $SO_X$ by a predetermined value or more.

BEST MODE FOR CARRYING OUT THE INVENTION

Figure 1:
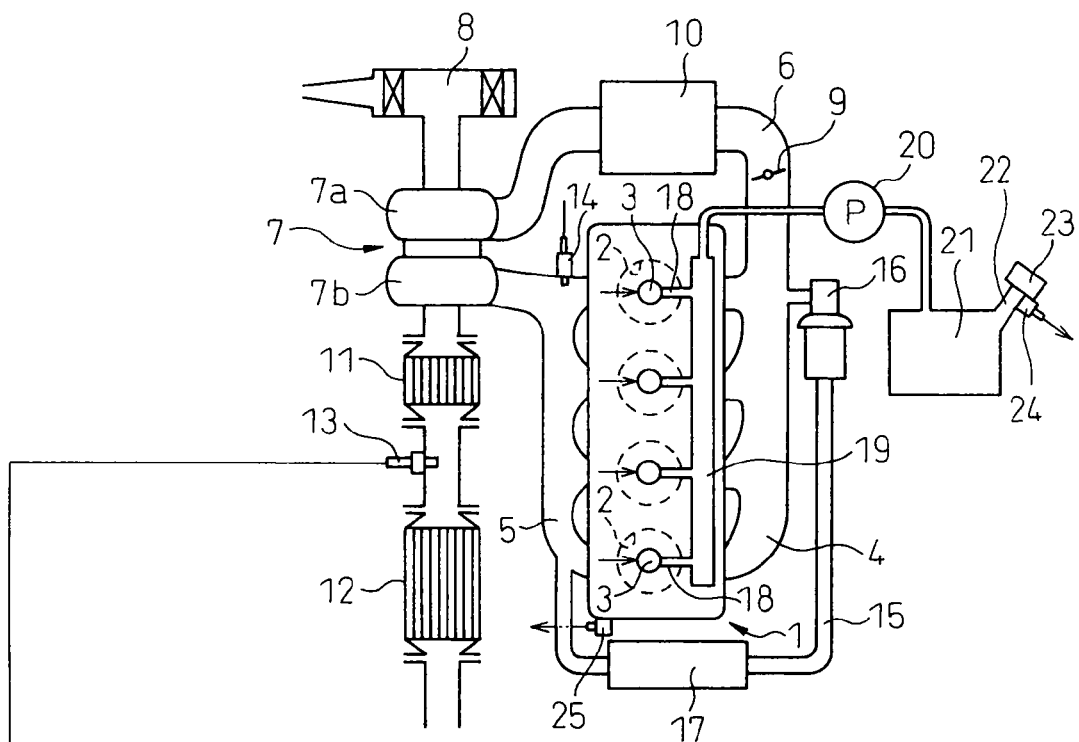
FIG. 1 is a view showing a compression ignition type internal combustion engine.
Figure 1:
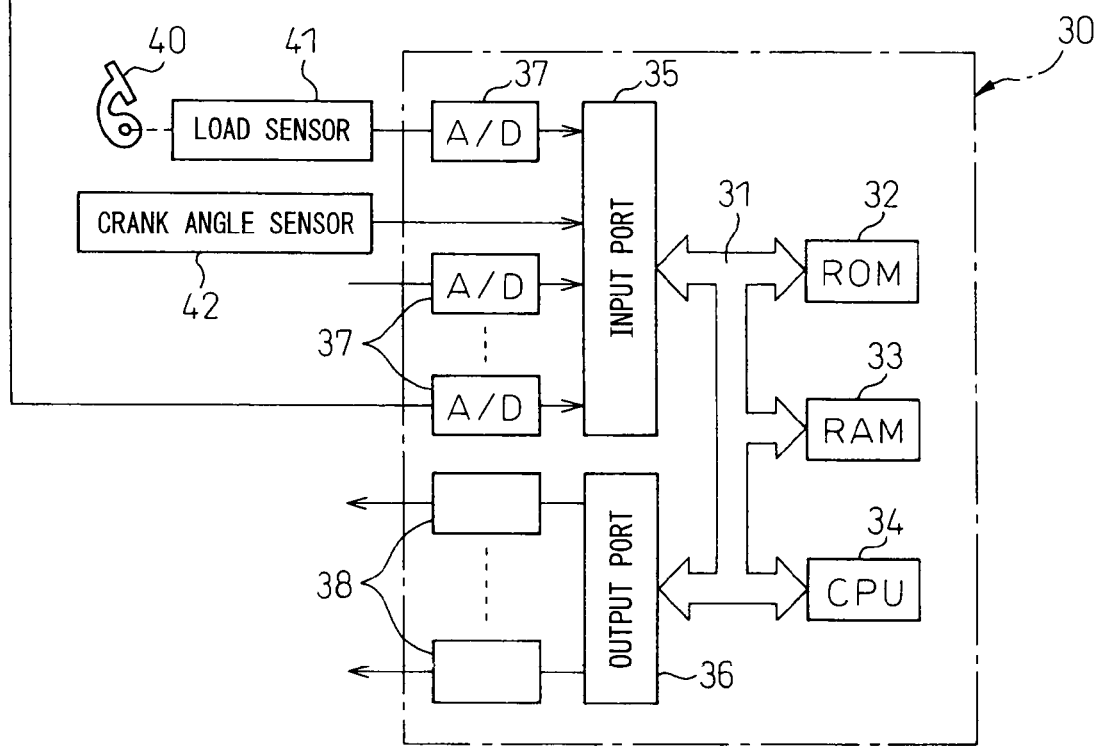

FIG. 1 shows an overview of a compression ignition type internal combustion engine.

Referring to FIG. 1, 1 indicates an engine body, 2 a combustion chamber of each cylinder, 3 an electronic control type fuel injector for injecting fuel into each combustion chamber 2, 4 an intake manifold, and 5 an exhaust manifold. The intake manifold 4 is connected through an intake duct 6 to an outlet of a compressor 7a of an exhaust turbocharger 7. The inlet of the compressor 7a is connected to an air cleaner 8. Inside the intake duct 6, a throttle valve 9 driven by a step motor is arranged. Further, around the intake duct 6, a cooling device 10 for cooling the intake air flowing through the inside of the intake duct 6 is arranged. In the embodiment shown in FIG. 1, the engine coolant is guided inside the cooling device 10 where the engine coolant cools the intake air.

On the other hand, the exhaust manifold 5 is connected to the inlet of an exhaust turbine 7b of an exhaust turbocharger 7. The outlet of the exhaust turbine 7b is connected to the inlet of the $SO_X$ trap catalyst 11. Further, the outlet of the $SO_X$ trap catalyst 11 is connected to an $NO_X$ storing catalyst 12. As shown in FIG. 1, downstream of the $SO_X$ trap catalyst 11, an $SO_X$ sensor 13 is arranged for detecting the sulfur component contained in the exhaust gas, that is, the $SO_X$. Further, inside the exhaust manifold 5, a fuel addition valve 14 is arranged for adding fuel into the exhaust gas.

The exhaust manifold 5 and the intake manifold 4 are connected to each other through an exhaust gas recirculation (hereinafter referred to as "EGR") passage 15. Inside the EGR passage 15, an electronic control type EGR control valve 16 is arranged. Further, around the EGR passage 15, a cooling device 17 is arranged for cooling the EGR gas flowing through the inside of the EGR passage 15. In the embodiment shown in FIG. 1, engine coolant is guided to the inside of the cooling device 17 where the engine coolant cools the EGR gas. On the other hand, the fuel injectors 3 is connected through fuel feed pipes 18 to a common rail 19. Fuel in the fuel tank 21 is fed to the common rail 19 by an electronic control type variable discharge fuel pump 20. The fuel fed into the common rail 19 is fed through the fuel feed pipes 18 to the fuel injectors 3.

A fuel refill port 22 of the fuel tank 21 is usually closed by a fuel cap 23. This fuel cap 23 is removed when refilling the fuel tank 21 with fuel. The fuel refill port 22 is provided with a sensor 24 for detecting when the fuel cap 23 has been removed. Further, the engine body 1 is provided with a level sensor 25 for detecting the oil level of the lubrication oil. At the time of oil change, the old oil is drained and new oil is supplied, so the oil level changes at this time. In the embodiment shown in FIG. 1, whether or not the oil has been changed is judged based on the detection signal of the level sensor 25.

An electronic control unit 30 is comprised of a digital computer provided with a ROM (read only memory) 32, RAM (random access memory) 33, CPU (microprocessor) 34, input port 35, and output port 36 all connected to each other by a bidirectional bus 31. As shown in FIG. 1, an accelerator pedal 40 is connected to a load sensor 41 generating an output voltage proportional to the depression amount L of the accelerator pedal 40. The output voltages of these sensors 13, 24, and 25 and this load sensor 41 are input through corresponding AD converters 37 to the input port 35. Further, the input port 35 has a crank angle sensor 42 generating an output pulse every time the crank shaft rotates by for example 15° connected to it. On the other hand, the output port 36 is connected to the fuel injectors 3, step motor for driving the throttle valve 9, fuel addition valve 14, EGR control valve 16, and fuel pump 20 through the corresponding drive circuits 38.

First, explaining the $NO_X$ storing catalyst 12 shown in FIG. 1, this $NO_X$ storing catalyst 12 has the function of absorbing the $NO_X$ when the air-fuel ratio of the exhaust gas is lean and releasing the absorbed $NO_X$ when the exhaust gas becomes a stoichiometric or rich air-fuel ratio. In a compression ignition type internal combustion engine, the air-fuel ratio of the exhaust gas is lean, therefore usually the $NO_X$ contained in the exhaust gas is stored in the $NO_X$ storing catalyst 12.

In this regard, if the fuel continues being burned under a lean air-fuel ratio in this way, eventually the $NO_X$ storing catalyst 12 ends up becoming saturated in $NO_X$ storage ability and therefore the $NO_X$ storing catalyst 12 can no longer absorb the $NO_X$. Therefore, in the embodiment shown in FIG. 1, before the $NO_X$ storing catalyst 12 becomes saturated in storage ability, for example fuel is injected into the combustion chamber 2 during the exhaust stroke or fuel is added into the exhaust gas from the fuel addition valve 14 so as to temporarily make the air-fuel ratio of the exhaust gas rich and thereby make the $NO_X$ storing catalyst 12 release $NO_X$.

In this regard, the exhaust gas contains $SO_X$, that is, $SO_2$. If this $SO_2$ flows into the $NO_X$ storing catalyst 12, this $SO_2$ is stored in the $NO_X$ storing catalyst 12. In this case, if the amount of stored $SO_X$ increases, the amount of $NO_X$ which the $NO_X$ storing catalyst 12 can store will gradually fall. Therefore, in the embodiment shown in FIG. 1, an $SO_X$ trap catalyst 11 is arranged upstream of the $NO_X$ storing catalyst 12 and this $SO_X$ trap catalyst 11 is used to trap the $SO_X$ contained in the exhaust gas to thereby control the flow of $SO_X$ into the $NO_X$ storing catalyst 12.

In this regard, the amount of $SO_X$ contained in the exhaust gas has a great effect on the $NO_X$ storage ability of the $NO_X$ storing catalyst 12, so it is necessary to monitor the amount of $SO_X$ contained in the exhaust gas. In this case, if the amount of $SO_X$ contained in the exhaust gas increases, the $NO_X$ storing catalyst 12 will rapidly fall in $NO_X$ storage ability, so it is necessary to detect if the amount of $SO_X$ contained in the exhaust gas increases.

In this regard, the typical case where the amount of $SO_X$ contained in the exhaust gas increases in this way is when fuel or oil with a higher sulfur concentration compared with the fuel or oil assumed to be used in advance is used. Therefore, in the present invention, the sulfur component in the exhaust gas is detected by the $SO_X$ sensor 13 and it is judged if fuel or oil with a high sulfur concentration was used based on the results of detection by this $SO_X$ sensor 13. Next, the method of detection of the sulfur component according to the present invention will be explained.

Figure 2:
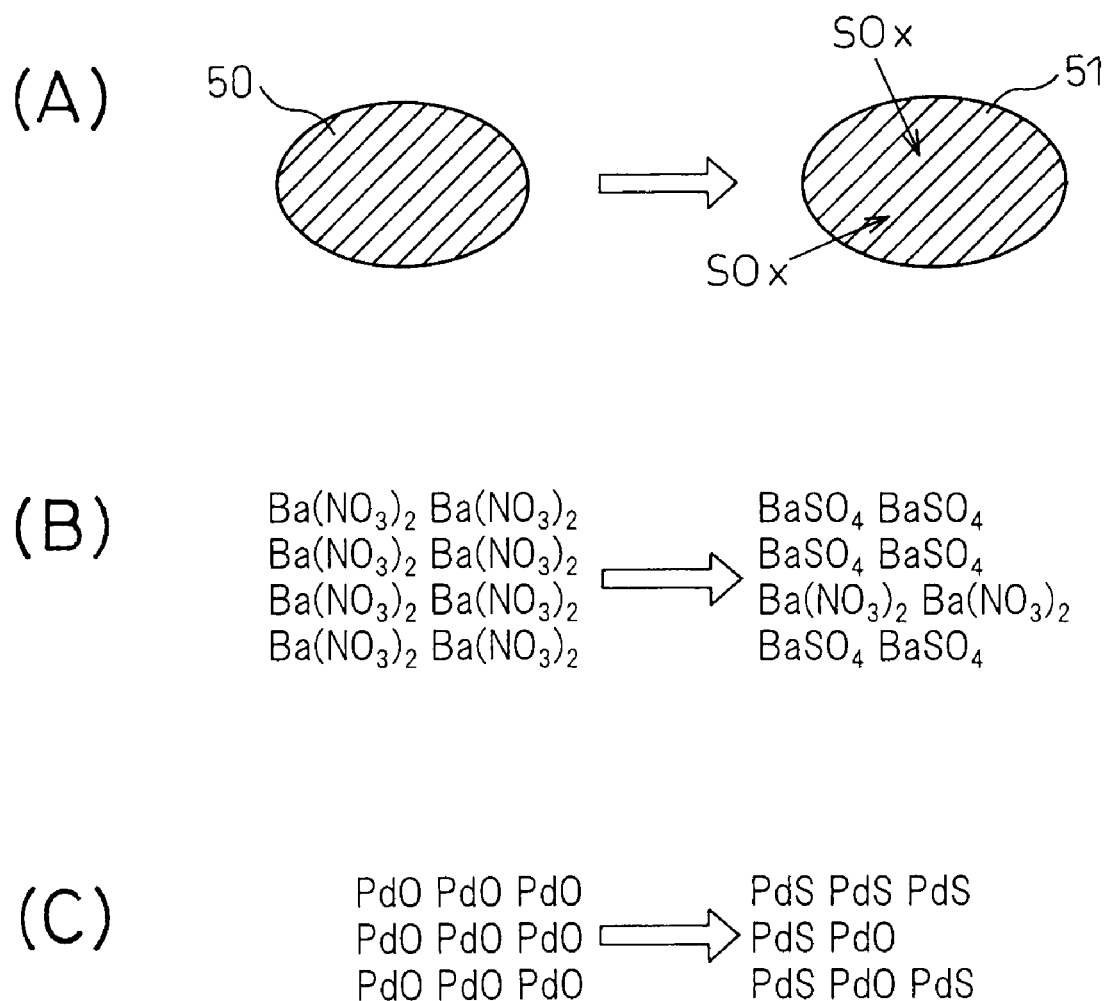
FIG. 2 is a view explaining the principle of detection of sulfur.

FIG. 2 shows the principle of detection of the sulfur component according to the present invention. In the present invention, in the flow path of the exhaust gas, a metal or metal compound able to trap the sulfur component in the exhaust gas, in the embodiment shown in FIG. 1, a metal or metal compound able to trap the $SO_X$ in the exhaust gas is arranged. The metal or metal compound is schematically shown by the notation 50 in FIG. 2(A). The metal or metal compound 50 shown in FIG. 2(A) is comprised of a metal or metal compound not including sulfur. In this embodiment of the present invention, this metal or metal compound 50 is comprised of an alkali metal, alkali earth metal, rare earth metal, precious metal, or compounds of these metals.

Next, the method of detection of the sulfur component will be explained taking as an example the case of using, as this metal or metal compound 50, an alkali earth metal, that is, barium Ba, or its compound.

Barium Ba becomes barium oxide BaO in the atmosphere. This barium oxide BaO is immediately changed to barium carbonate $BaCO_3$ by the CO or $CO_2$ contained in the exhaust gas when placed in the exhaust gas. Further, this barium carbonate $BaCO_3$ is changed to barium nitrate $Ba(NO_3)_2$ by the $NO_X$ contained in the exhaust gas.

That is, when barium Ba is used, the metal or metal compound 50 shown in FIG. 2(A) is barium oxide BaO, barium carbonate $BaCO_3$, or barium nitrate $Ba(NO_3)_2$. When this metal or metal compound 50 is placed in the exhaust gas, it becomes barium nitrate $Ba(NO_3)_2$. Expressed generally, the metal or metal compound 50 shown in FIG. 2(A) is comprised of an oxide, carbonate, or nitrate. When this metal or metal compound 50 is placed in the exhaust gas, the majority of it becomes a nitrate.

On the other hand, the exhaust gas contains a sulfur component, that is, $SO_X$, though smaller compared with the CO, HC, and $NO_X$. This $SO_X$ is trapped by the metal or metal compound 50 and, as shown in FIG. 2(A), changes to a metal compound 51 containing sulfur. When barium Ba is used, the metal compound 51 containing the sulfur is barium sulfate $BaSO_4$. Therefore, when the metal or metal compound 50 is placed in the exhaust gas, as shown in FIG. 2(B), part of the barium nitrate $Ba(NO_3)_2$ of the metal compound 50 comprised of the barium nitrate $Ba(NO_3)_2$ changes to barium sulfate $BaSO_4$. Expressed generally, part of the nitrate changes to a sulfate. In this case, the ratio of the sulfate in the metal compound 51 becomes higher along with the elapse of time, that is, the higher the amount of trapped sulfur component.

On the other hand, FIG. 2(C) shows the case where the metal or metal compound 50 is comprised of a precious metal or its compound. As this precious metal, palladium Pd, rhodium Rh, or platinum Pt can be used. As an example of FIG. 2(C), the case of use of palladium Pd is shown. In this case, if the sulfur component is trapped, the metal oxide PdO changes to the sulfide PdS.

If the nitrate changes to a sulfate or if the metal oxide changes to a sulfide, its properties change. Accordingly, the amount of trapped sulfur compound, that is, the amount of sulfur component in the gas, can be estimated from the change in these properties. Therefore, in the present invention, when the metal or metal compound 50 not containing sulfur changes to a metal compound 51 containing sulfur along with the elapse of time, a property of the metal compound 51 is measured and the sulfur component in the gas is detected from the measured property.

That is, in the present invention, in other words, when the amount of sulfur component trapped by the metal or metal compound 50 increases along with the elapse of time, a property of the metal or metal compound 50 changing along with the increase of the amount of the trapped sulfur component is measured and the sulfur component in the exhaust gas is detected from the measured property.

Next, referring to FIG. 3 to FIG. 6, the properties to be measured and the representative methods of detection corresponding to the properties to be measured will be explained. Note that FIG. 3 to FIG. 6 will be explained taking as an example the case of a nitrate changing to a sulfate as shown in FIG. 2(B).

Figure 3:
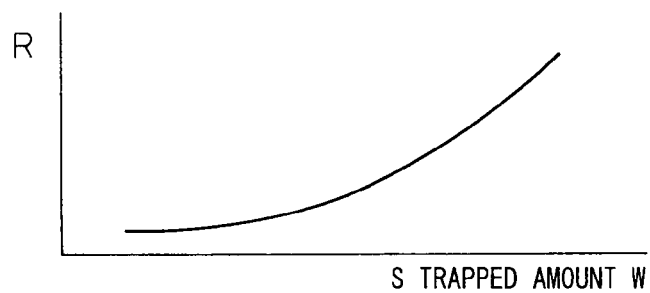
FIG. 3 is a view explaining the method of detection of sulfur.
Figure 3:
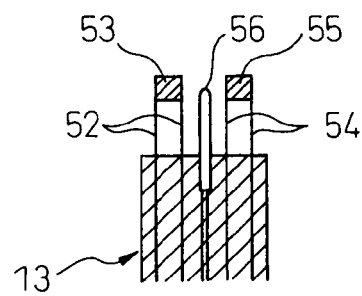
Figure 3:
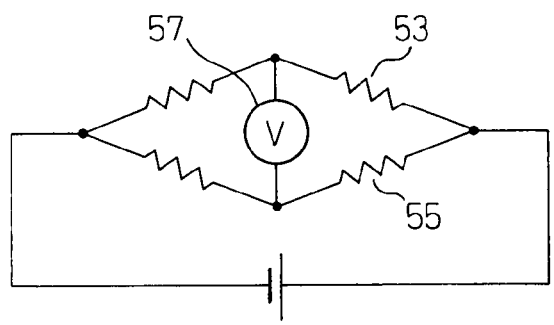
Figure 3:
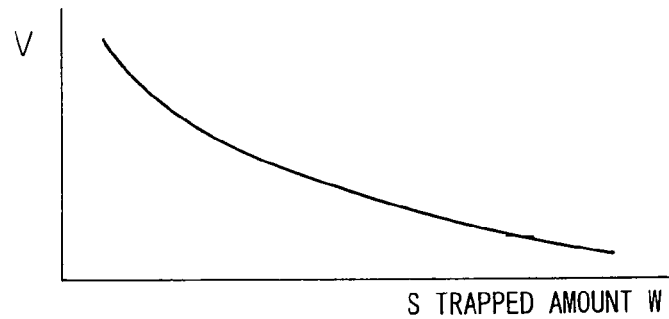

FIG. 3 shows a case where the property to be measured is an electrical property and shows a case where the measured electrical property is the electrical resistance.

FIG. 3(A) shows the relationship of the amount of trapped sulfur $SO_X$ and the electrical resistance value R. As shown in FIG. 3(A), the more the amount of trapped $SO_X$ increases, that is, the greater the amount of change of nitrates to sulfates, the greater the change in the electrical resistance value R. Accordingly, the amount of trapped $SO_X$, that is, the cumulative value of the amount of $SO_X$ in the exhaust gas, can be found from the electrical resistance value R.

FIG. 3(B) shows the detection part of the $SO_X$ sensor 13 shown in FIG. 1. As shown in FIG. 3(B), the detection part of the $SO_X$ sensor 13 arranged in the flow path of the exhaust gas is provided with a metal compound piece for detection 53 supported by a pair of terminals 52 and a metal compound piece for reference 55 supported by a pair of terminals 54. Further, this detection part of the $SO_X$ sensor 13 has a temperature sensor arranged at it. The metal compound piece for detection 53 is formed from an oxide, carbonate, or nitrate, while the metal compound piece for reference 55 is formed from a sulfate. When the exhaust gas flows, the metal compound piece for reference 55 will not change, but the metal compound piece for detection 53 changes to a nitrate when not a nitrate, then the $SO_X$ contained in the exhaust gas causes the nitrate to change to a sulfate little by little. Therefore, the electrical resistance value R of the metal compound piece for detection 53 gradually changes.

The electrical resistance value R of the metal compound piece for detection 53 becomes higher the higher the temperature of the surroundings. Therefore, the metal compound piece for reference 55 is provided to eliminate the effect of such a temperature change on the electrical resistance value R. For example, the Wheatstone bridge shown in FIG. 3(C) is used to find the amount of trapped $SO_X$ from the difference between the electrical resistance value of the metal compound piece for detection 53 and the electrical resistance value of the metal compound piece for reference 55. The voltage V appearing at the voltmeter 57 when using the Wheatstone bridge shown in FIG. 3(C), as shown in FIG. 3(D), falls as the amount of trapped $SO_X$ increases.

Figure 4:
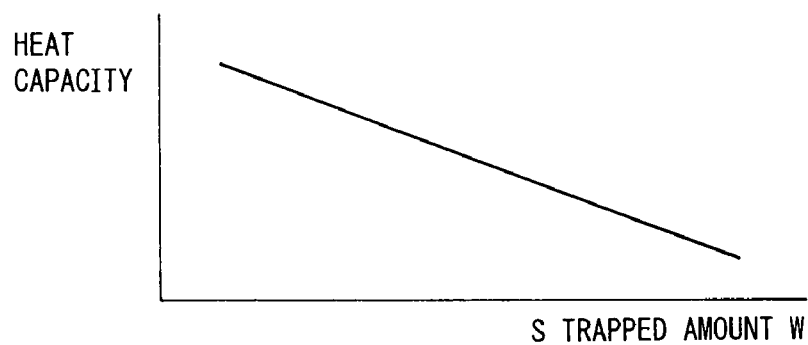
FIG. 4 is a view explaining the method of detection of sulfur.
Figure 4:
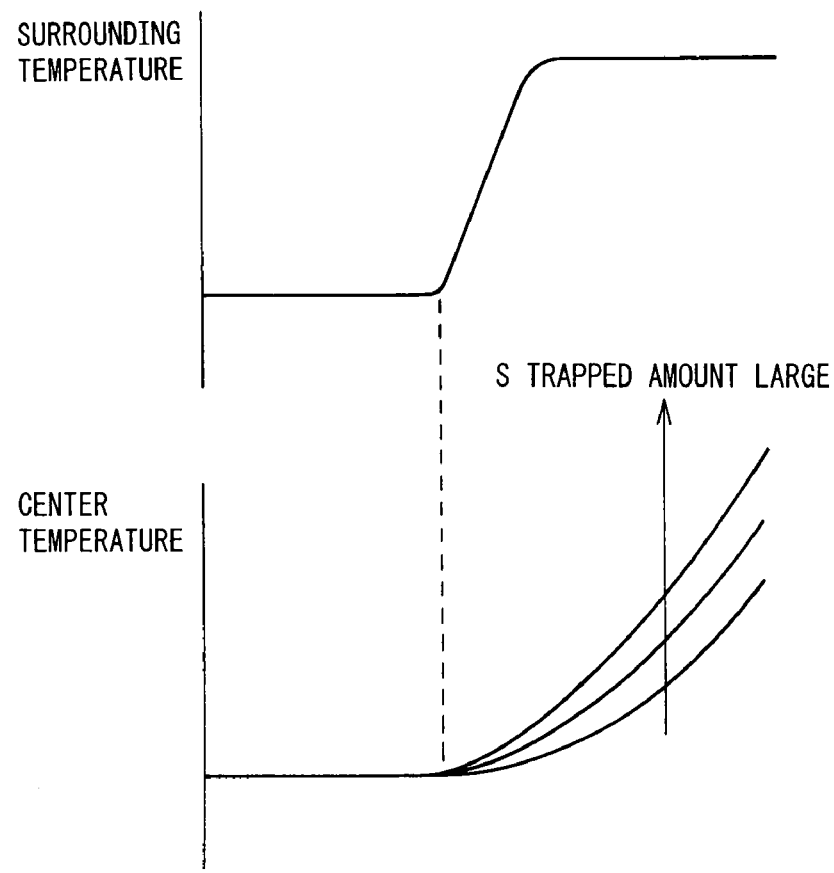
Figure 5:
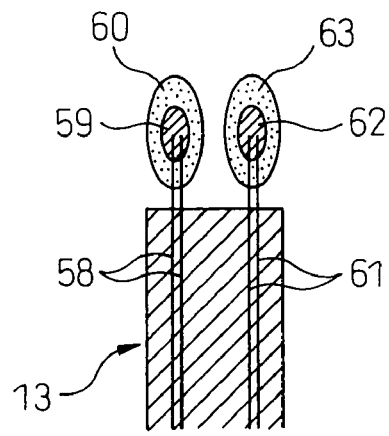
FIG. 5 is a view explaining the method of detection of sulfur.
Figure 5:
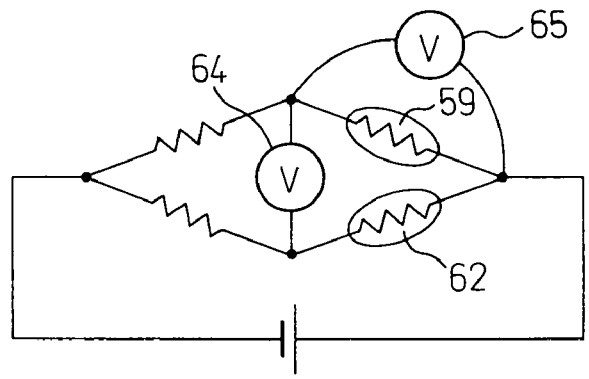
Figure 5:
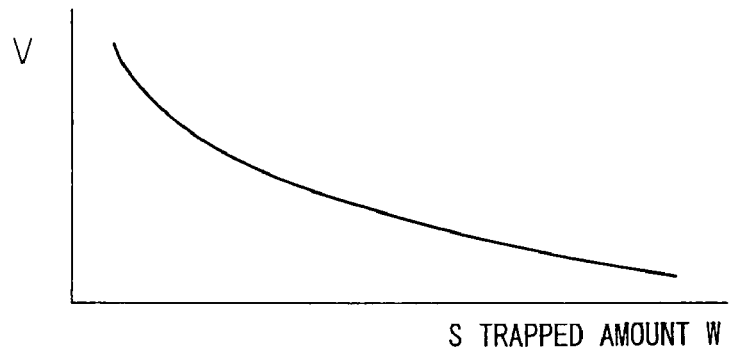
Figure 6:
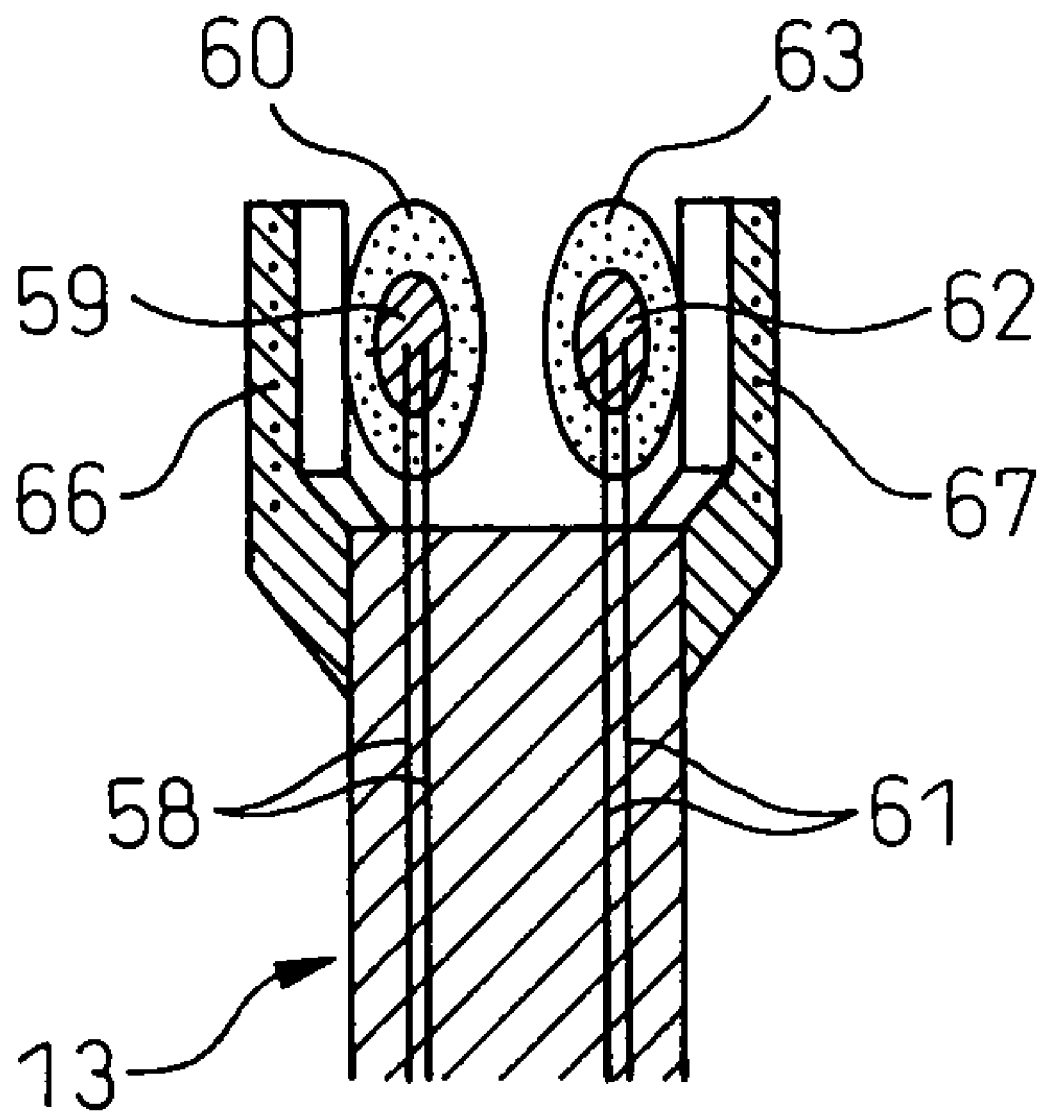
FIG. 6 is a view explaining the method of detection of sulfur.

FIG. 4 to FIG. 6 show cases where the measured property is a thermal property and where the measured thermal property is the heat capacity and thermal conductivity.

As shown in FIG. 4(A), the more the amount of trapped $SO_X$ increases, the more the heat capacity of the metal compound piece decreases. Accordingly, as shown in FIG. 4(B), when the temperature around the metal compound piece rises, the rate of increase of the center temperature of the metal compound piece rises the more the amount of trapped sulfur $SO_X$ increases.

FIG. 5(A) shows the detection part of the $SO_X$ sensor 13. In the example shown in FIG. 5(A), a thermistor element for detection 59 having a pair of lead wires 58 and a thermistor element for reference 62 having a pair of lead wires 61 are arranged. Further, in this example, the surroundings of the thermistor element for detection 59 are surrounded by a metal compound for detection 60, and the surroundings of the thermistor element for reference 62 are surrounded by a metal compound for reference 63.

In this example, the heat capacity of the metal compound for detection 60 is estimated from the response of the change in the resistance value of the thermistor element for detection 59 when the temperature around the metal compound for detection 60 changes, the heat capacity of the metal compound for reference 63 is estimated from the response of the change in the resistance value of the thermistor element for reference 62 when the temperature around the metal compound for reference 63 changes, and the amount W of trapped $SO_X$ is found from the difference of these heat capacities.

That is, specifically, a Wheatstone bridge such as shown in FIG. 5(B) is used to find the difference between the resistance value of the thermistor element for detection 59 and the resistance value of the thermistor element for reference 62 in the form of voltage. In this case, the voltage V of the voltmeter 64 showing the difference of resistance values falls, as shown in FIG. 5(C), the more the sulfur S trapped at the metal compound for detection 60 increases. Further, the temperature of the metal compound for detection 63 is detected from the voltage of the voltmeter 65.

On the other hand, in the example shown in FIG. 6, the metal compound for detection 60 and the metal compound for reference 63 are respectively provided with heaters 66 and 67 for heating. In this example, by operating the heaters 66 and 67, it is possible to raise the temperatures of the metal compound for detection 60 and metal compound for reference 63.

Next, the method of detection of the concentration of sulfur in fuel or oil will be explained while referring to FIGS. 7(A) and (B) schematically showing changes in the amount of trapped sulfur along with time. Note that in FIG. 7(A), (B), the solid line WX shows the assumed trapped amount of $SO_X$ when assuming that fuel or oil of the sulfur concentration assumed in advance is being used, while the broken line W shows the actual amount of trapped $SO_X$ detected by the $SO_X$ sensor 13. Note that when fuel or oil of the sulfur concentration assumed in advance is being used, if the operating state of the engine is determined, the amount of $SO_X$ exhausted from the engine is determined, so the assumed trapped amount WX is calculated based on the operating state of the engine.

Figure 7:
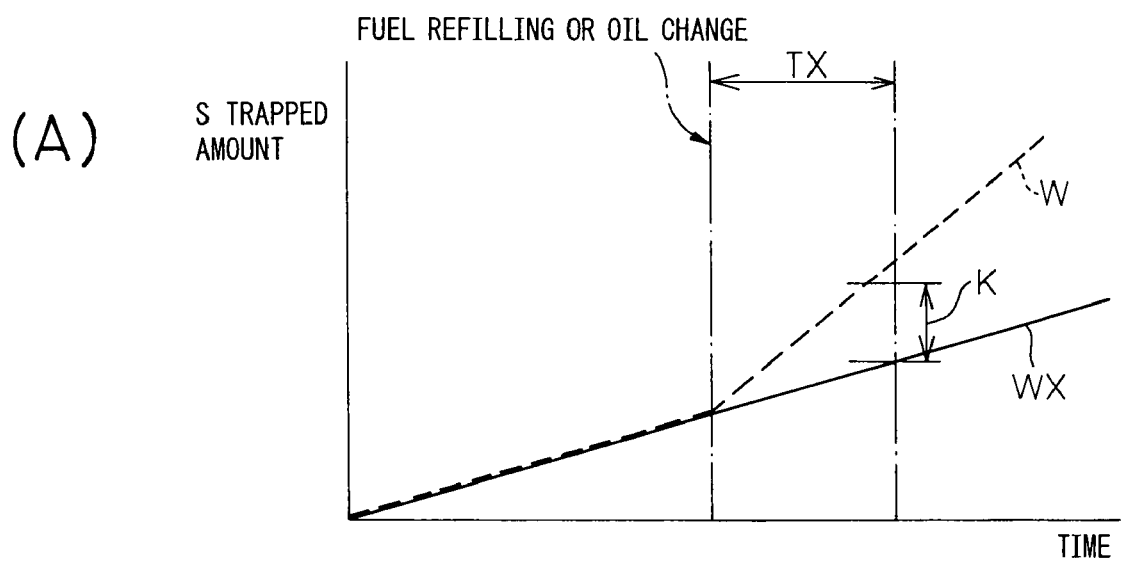
FIG. 7 is a time chart showing changes in the amount of trapped a sulfur component.
Figure 7:
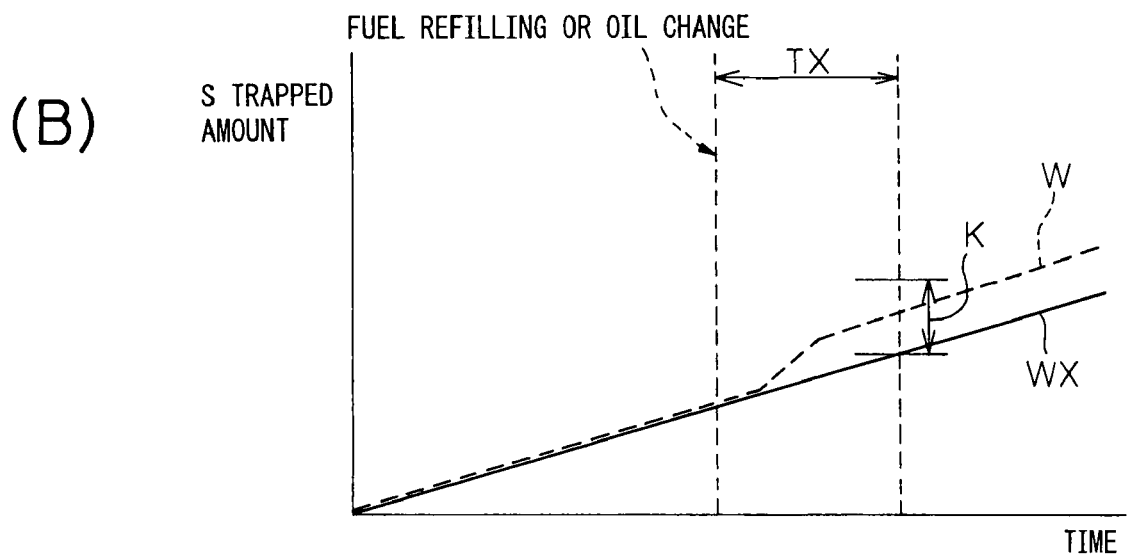

Now, if fuel of a sulfur concentration higher than the sulfur concentration assumed for the time of refilling the fuel is refilled or oil of a sulfur concentration higher than the sulfur concentration assumed for the time of oil change is supplied, the amount of $SO_X$ contained in the exhaust gas will rapidly increase, so as shown by the broken line in FIG. 7(A), the actual amount W of trapped $SO_X$ will rapidly increase from the assumed trapped amount WX of $SO_X$. Therefore when the actual trapped amount W of $SO_X$ becomes larger than the assumed trapped amount WX of $SO_X$ by a certain value or more, it is judged that fuel or oil with a high sulfur concentration was used.

On the other hand, FIG. 7(B) shows the case where for example the temperature of the exhaust gas temporarily becomes extremely high and the $SO_X$ trap catalyst 11 releases $SO_X$. In this case, as shown by the broken line in FIG. 7(B), while the $SO_X$ trap catalyst 11 is releasing $SO_X$, the actual trapped amount W of $SO_X$ temporarily increases from the assumed trapped amount WX. Therefore, as will be understood from FIG. 7(A), (B), if setting in advance a value K larger than the increase of actual trapped amount W from the assumed trapped amount WX when $SO_X$ is released from the $SO_X$ trap catalyst 11 and smaller than the increase of the actual trapped amount W from the assumed trapped amount WX when fuel or oil of a high sulfur concentration is used, it can be judged that fuel or oil with a high sulfur concentration has been used when the actual trapped amount W of $SO_X$ becomes larger than the assumed trapped amount WX of $SO_X$ by this value K or more.

In this regard, the cumulative value of the amount of $SO_X$ contained in the exhaust gas is proportional to the amount of trapped $SO_X$ shown by W or WX. Therefore, in the present invention, if expressed generally, the actual cumulative value of the amount of $SO_X$ actually contained in the exhaust gas is calculated from the detected amount of sulfur component, the assumed cumulative value of the amount of $SO_X$, assumed to be contained in the exhaust gas based on the operating state of the engine based on the assumption that fuel or oil of the sulfur concentration assumed in advance is being used, is calculated, and it is judged that fuel or oil of a sulfur concentration higher than the sulfur concentration assumed in advance is being used when the actual cumulative value of the amount of $SO_X$ becomes higher than the assumed cumulative value of the amount of $SO_X$ by a predetermined value K or more.

Note that in the embodiment shown in FIG. 7(A), (B), the actual cumulative value of the amount of $SO_X$ and the assumed cumulative value of the amount of $SO_X$ are made the cumulative values in a predetermined time period TX. Further, in the embodiment shown in FIG. 7(A), (B), when fuel is refilled or when oil is changed, this predetermined time period TX starts to advance. In doing this, it can be judged that fuel of a high sulfur concentration was used or oil of a high sulfur concentration was used.

Figure 8:
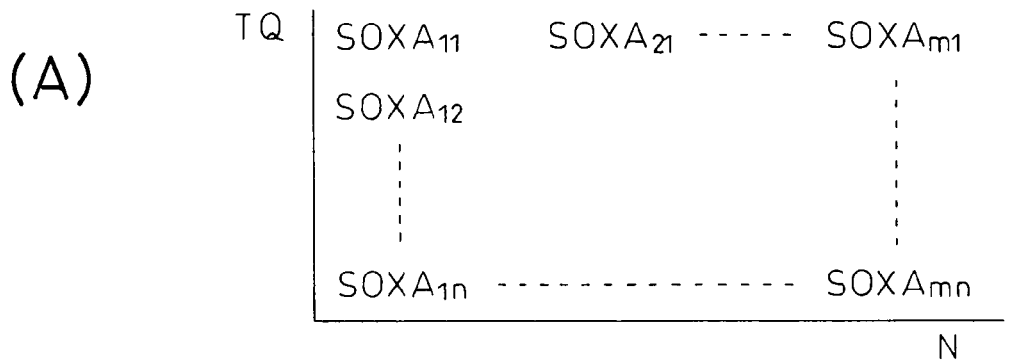
FIG. 8 is a view showing a map of the amount of $SO_X$ exhausted from an engine.
Figure 8:
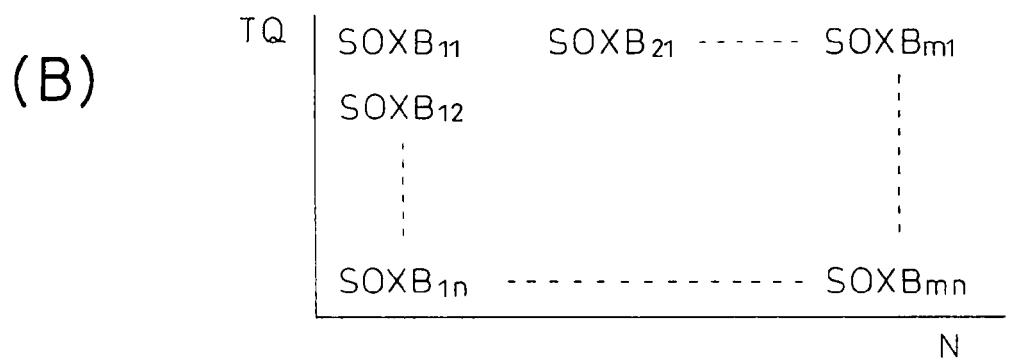

Next, the method of finding the assumed trapped amount WX of $SO_X$ will be explained with reference to FIG. 8 and FIG. 9.

When fuel with a sulfur concentration assumed in advance is used, the amount of the sulfur component exhausted from the engine is proportional to the amount of fuel injection. The amount of fuel injection is a function of the required torque and engine speed. Therefore, the amount of the sulfur component exhausted from the engine also becomes a function of the required torque and engine speed. In this embodiment of the present invention, the amount SOXA of the sulfur component exhausted from the engine per unit time is stored as a function of the required torque TQ and engine speed N in the form of the map shown in FIG. 8(A) in advance in the ROM 32.

Further, when lubrication oil of a sulfur concentration assumed in advance is used, the amount of oil which can be burned in the combustion chamber 2, that is, the amount of the sulfur component exhausted from the engine, also becomes a function of the required torque and engine speed. In this embodiment of the present invention, the amount SOXB of the sulfur component contained in the oil and exhausted from the engine per unit time is stored as a function of the required torque TQ and engine speed N in the form of the map shown in FIG. 8(B) in advance in the ROM 32. By cumulatively adding the sum of the amounts SOXA and SOXB of these sulfur components, the cumulative amount $\Sigma$SOX of the sulfur component exhausted from the engine is calculated.

Figure 9:
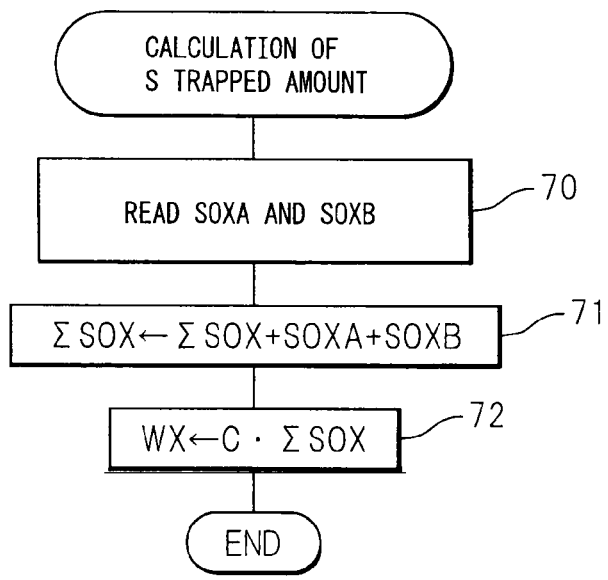
FIG. 9 is a flow chart for calculation of the assumed amount of trapped $SO_X$.

FIG. 9 shows the routine for calculating the assumed trapped amount WX of the sulfur component in the case where fuel or oil of a sulfur concentration assumed in advance is being used. This routine is executed by interruption every predetermined time interval.

Referring to FIG. 9, first, at step 70, the amounts SOXA and SOXB of the sulfur component exhausted from the engine per unit time are read from FIG. 8(A), (B). Next, at step 71, the sum of SOXA and SOXB is added to the amount $\Sigma$SOX of the sulfur component. On the other hand, the assumed trapped amount WX of the sulfur component considered to be trapped at the detection metal compound 53, 60 is proportional to the cumulative amount $\Sigma$SOX of the sulfur component exhausted from the engine. Therefore, at step 72, by multiplying the cumulative amount $\Sigma$SOX of the sulfur component exhausted from the engine with a proportional constant C, the assumed trapped amount WX of the sulfur component considered to be trapped in the detection metal compound 53, 60 is calculated.

Figure 10:
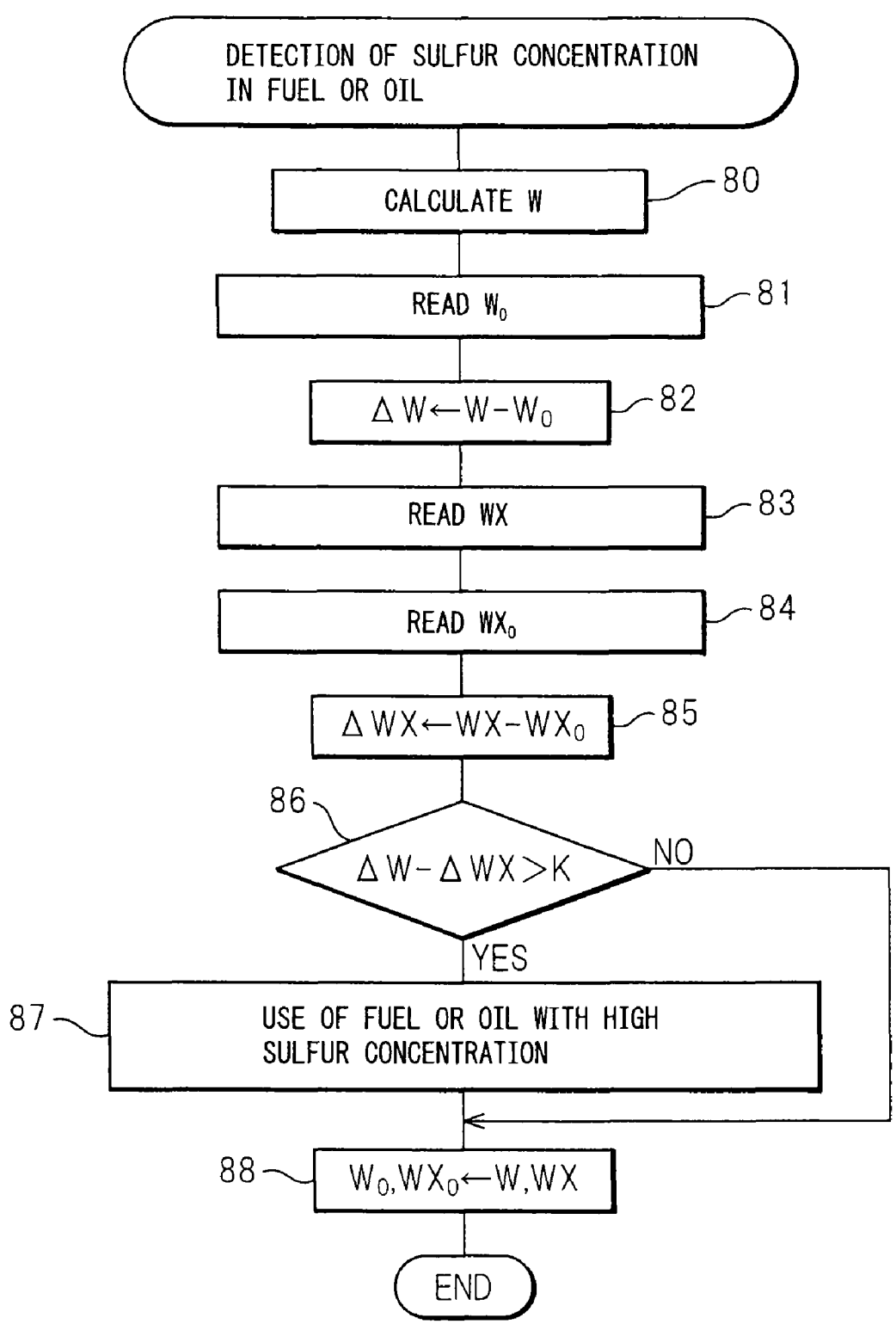
FIG. 10 is a flow chart for detection of the sulfur concentration in fuel and oil.

FIG. 10 shows the routine for detection of the concentration of sulfur in the fuel or oil in the present invention. This routine is executed by interruption every predetermined time interval.

Referring to FIG. 10, first, at step 80, the actual trapped amount W of $SO_X$ is calculated from the detected value of the $SO_X$ sensor 13. Next, at step 81, the actual trapped amount $W_0$ of $SO_X$ at the previous interruption is read. Next, at step 82, the increase $\Delta W(=W-W_0)$ of the actual trapped amount of $SO_X$ from the previous interruption to the current interruption is calculated.

Next, at step 83, the current assumed trapped amount WX of $SO_X$ calculated at the routine shown in FIG. 9 is read. Next, at step 84, the assumed trapped amount $WX_0$ of $SO_X$ at the time of the previous interruption is read. Next, at step 85, the increase $\Delta WX(=WX-WX_0)$ of the assumed trapped amount of $SO_X$ from the previous interruption to the current interruption is calculated.

Next, at step 86, it is judged if the increase $\Delta W$ of the actual trapped amount of $SO_X$ is larger than the increase $\Delta WX_0$ of the assumed trapped amount of $SO_X$ by a predetermined value K shown in FIG. 7(A), (B) or more, that is, if $\Delta W - \Delta WX > K$. When $\Delta W - \Delta WX > K$, the routine proceeds to step 87 where it is judged that fuel or oil with a high sulfur concentration is being used. Next, at step 88, W is stored as $W_0$ and WX is stored as $WX_0$.

Figure 11:
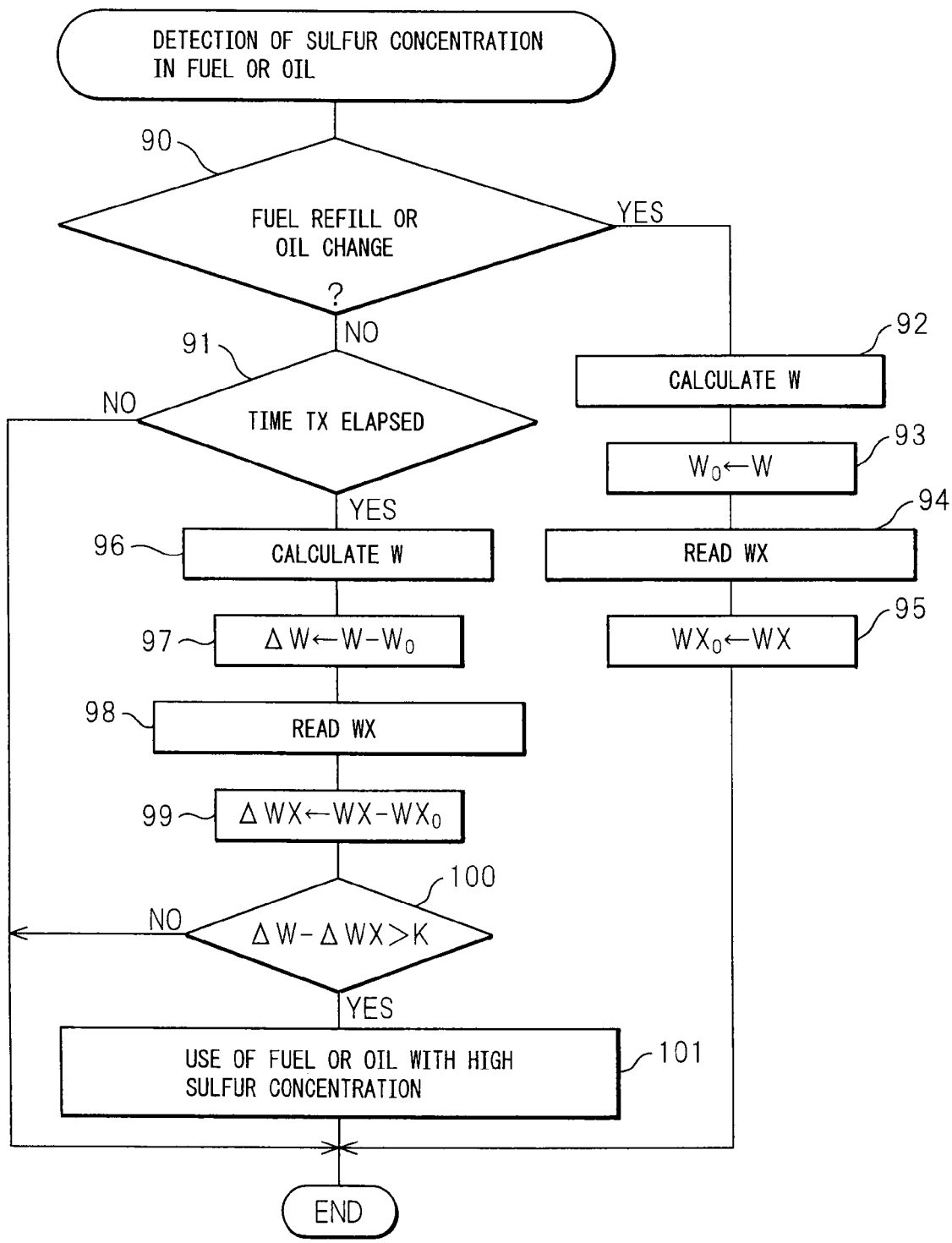
FIG. 11 is a flow chart for detection of the sulfur concentration in fuel and oil.

FIG. 11 shows a routine of another embodiment for detecting the concentration of sulfur in the fuel or oil. This routine is also executed by interruption every predetermined time interval.

In this embodiment, as shown in FIG. 7(A), (B), when a certain time period TX has elapsed from when the fuel was refilled or the oil was changed and the actual trapped amount W of $SO_X$ becomes larger than the assumed trapped amount WX of $SO_X$ by a predetermined value K, it is judged that fuel or oil with a high sulfur concentration was used.

That is, referring to FIG. 11, first, at step 90, it is judged if fuel has been refilled or oil has been changed based on the detection signals of the sensor 24 and level sensor 25. When neither fuel has been refilled nor oil has been changed, the routine proceeds to step 91 where it is judged if a predetermined time period TX has elapsed from when fuel was refilled or oil was changed. When neither fuel has been refilled nor oil has been changed, the processing cycle is ended.

On the other hand, when it is judged at step 90 that fuel has been refilled or the oil has been changed, the routine proceeds to step 92 where the actual trapped amount W of $SO_X$ is calculated from the detected value of the $SO_X$ sensor 13. Next, at step 93, this actual trapped amount W is stored as $W_0$.

Next, at step 94, the current assumed trapped amount WX of $SO_X$ calculated by the routine shown in FIG. 9 is read. Next, at step 95, this assumed trapped amount WX is stored as $WX_0$.

At the next interruption, the routine proceeds from step 90 to step 91. If a certain time period TX has elapsed from when the fuel is refilled or oil is changed, the routine proceeds to step 96. At step 96, the $SO_X$ actual trapped amount W is calculated from the detected value of the $SO_X$ sensor 13. Next, at step 81, the increase $\Delta W(=W-W_0)$ of the actual trapped amount of $SO_X$ during the time period TX is calculated. Next, at step 98, the current assumed trapped amount WX of $SO_X$ calculated in the routine shown in FIG. 9 is read. Next, at step 99, the increase $\Delta WX(=WX-WX_0)$ of the assumed trapped amount of $SO_X$ in the time period TX is calculated.

Next, at step 100, it is judged if the increase $\Delta W$ of the actual trapped amount of $SO_X$ has become larger than the increase $\Delta WX_0$ of the assumed trapped amount of $SO_X$ by a preset value K shown in FIG. 7(A), (B) or more, that is, $\Delta W - \Delta WX > K$. When $\Delta W - \Delta WX > K$, the routine proceeds to step 101 where it is judged if fuel or oil with a high sulfur concentration is being used.

Figure 12:
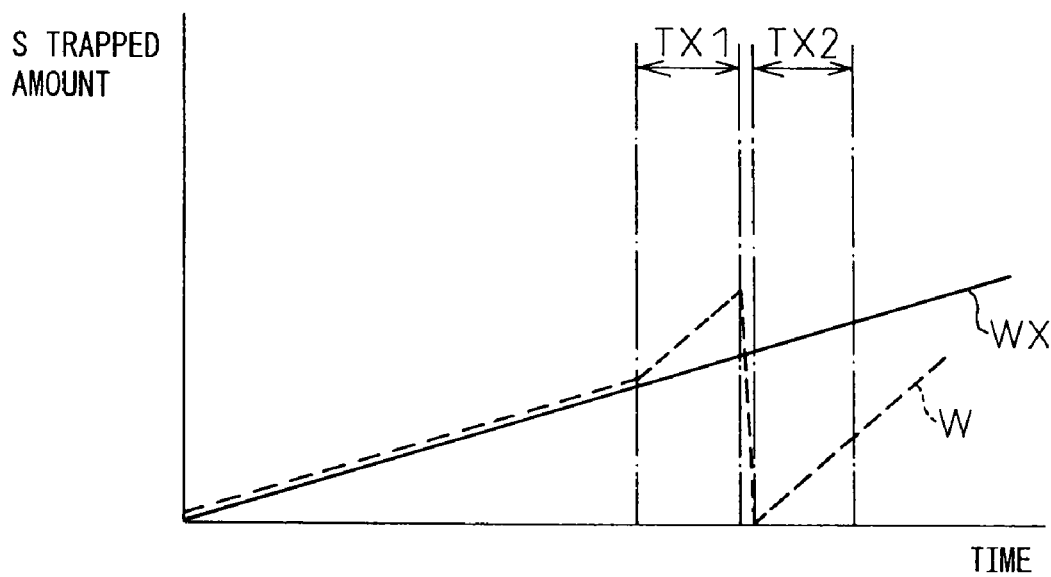
FIG. 12 is a time chart showing changes in the amount of trapped sulfur component.
Figure 12:
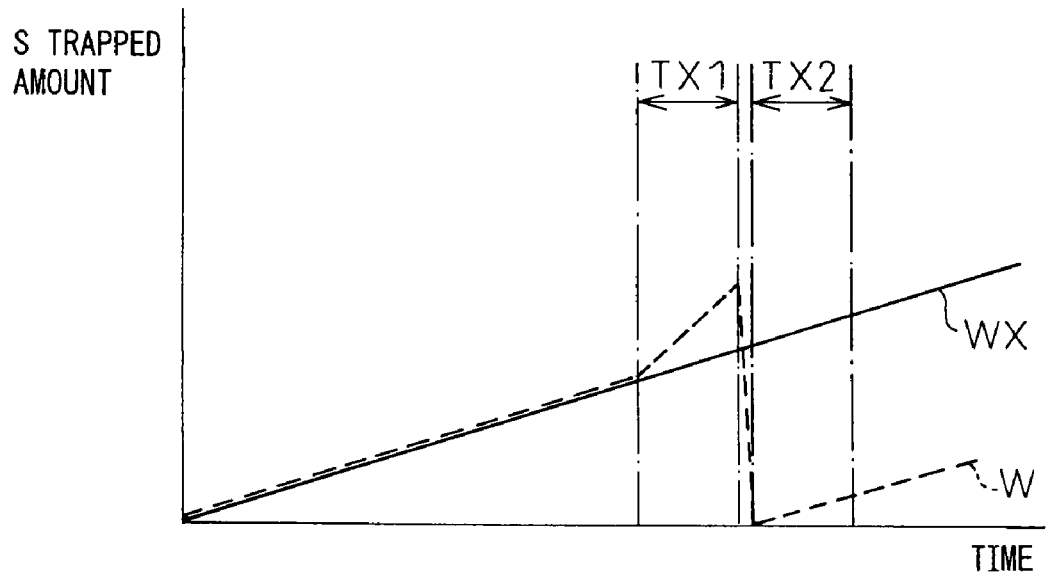
Figure 13:
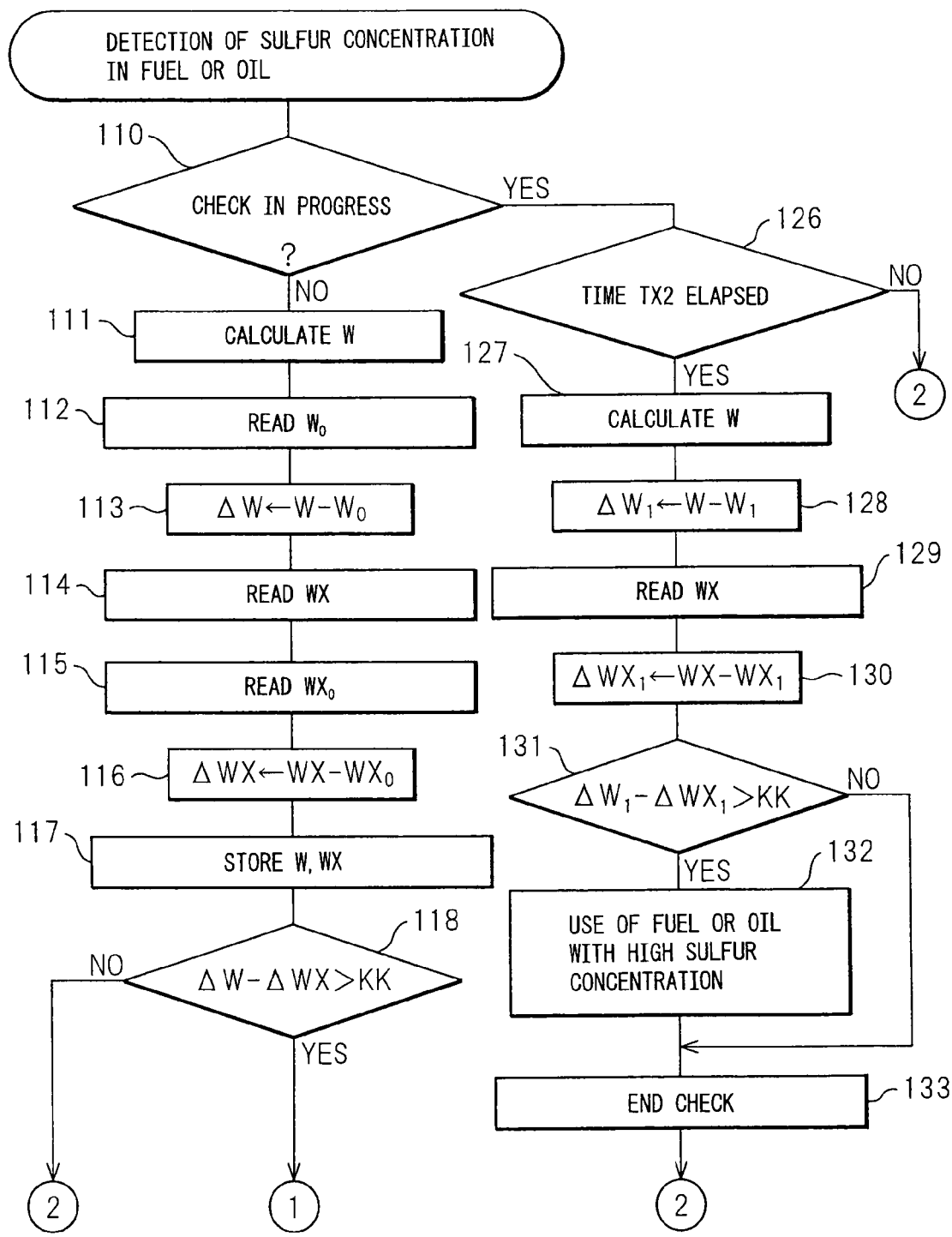
FIG. 13 is a flow chart for detection of the sulfur concentration in fuel and oil.
Figure 14:
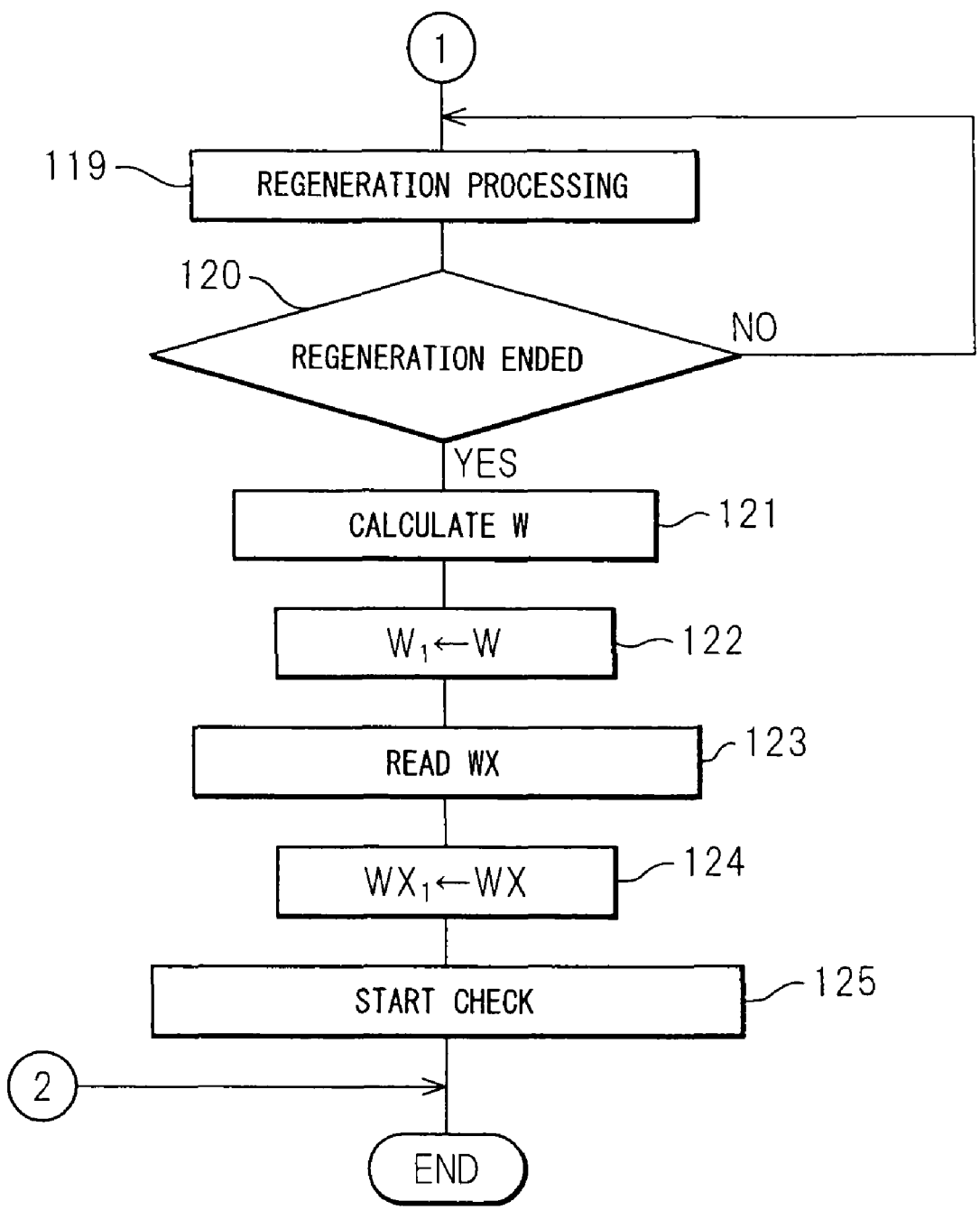
FIG. 14 is a flow chart for detection of the sulfur concentration in fuel and oil.

FIG. 12 to FIG. 14 show still a further embodiment of the present invention.

As explained above, the actual trapped amount W of $SO_X$ increases when fuel or oil with a high sulfur concentration is used and increases even when the $SO_X$ trap catalyst 11 releases $SO_X$. Therefore in this embodiment, to differentiate between the case where the actual trapped amount increases due to using fuel or oil with a high sulfur concentration and the case where the actual trapped amount W increases due to the $SO_X$ trap catalyst 11 releasing $SO_X$, processing is performed for regeneration to remove the sulfur component trapped at the metal compound for detection 53, 60 when the actual trapped amount W of $SO_X$ increases and it is judged if fuel or oil with a high sulfur concentration has been used from the change in the actual trapped amount W of $SO_X$ after this regeneration processing.

In this embodiment of the present invention, this regeneration treatment is for example performed as follows. That is, the metal compounds for detection 53, 60 have the property of releasing the sulfur component at about 1300° C. or more where the sulfur breaks down by heat when the air-fuel ratio of the exhaust gas is lean and releasing the sulfur component at about 600° C. or more when the air-fuel ratio of the exhaust gas is rich.

Therefore, when it should be regenerated, for example, the temperature of the metal compound for detection 53, 60 is raised to the sulfur release temperature enabling release of the trapped sulfur component under a rich air-fuel ratio of the exhaust gas, that is, 600° C. or more, and making the air-fuel ratio of the exhaust gas rich in that state for regeneration. Alternatively, the temperature of the metal compound for detection 53, 60 is raised to the sulfur release temperature enabling release of the trapped sulfur component under a lean air-fuel ratio of the exhaust gas, that is, 1300° C. or more, for regeneration.

Note that in this case, when using as the $SO_X$ sensor 13 the $SO_X$ sensor with a heater shown in FIG. 6 and the temperature of the metal compound for detection 53, 60 reaches a temperature somewhat lower than the sulfur release temperature, the heaters 66, 67 can be operated to raise the temperature of the metal compound for detection 53, 60 to the sulfur release temperature and thereby regenerate the metal compound for detection 53, 60.

That is, in this embodiment, when the actual cumulative value of the amount of $SO_X$ becomes larger than the assumed cumulative value of the amount of $SO_X$ by a predetermined value or more, specifically, as shown in FIG. 12(A), (B), the increase of the actual trapped amount W of $SO_X$ in a predetermined time period TX1 becomes higher than the increase of the assumed trapped amount WX of $SO_X$ by a predetermined value or more, the metal compound for detection 53, 60 is processed for regeneration. After the regeneration processing, the actual trapped amount W of $SO_X$ falls.

When fuel or oil with a high sulfur concentration is used, as shown in FIG. 12(A), the rate of increase of the actual trapped amount W of $SO_X$ after regeneration processing becomes larger than the rate of increase of the assumed trapped amount WX of $SO_X$ as before the regeneration processing. As opposed to this, when the $SO_X$ trap catalyst 11 has temporarily released the $SO_X$, as shown in FIG. 12(B), the rate of increase of the actual trapped amount W of the amount of $SO_X$ after the regeneration processing becomes substantially equal to the rate of increase of the assumed trapped amount WX of amount of $SO_X$.

Therefore, in this embodiment, when it is judged that the increase of the actual cumulative value of the amount of $SO_X$ is larger than the increase of the assumed cumulative value of the amount of $SO_X$ after the regeneration processing, it is judged that fuel or oil of a sulfur concentration higher than a sulfur concentration assumed in advance is used.

FIG. 13 and FIG. 14 show the routine for detection of the concentration of sulfur in the fuel or oil for working this embodiment. This routine is also executed by interruption every predetermined time interval.

Referring to FIG. 13 and FIG. 14, first, at step 110, it is judged if a check of the reason for increase of the actual trapped amount of $SO_X$ after the regeneration processing is in progress. When the check is not in progress, the routine proceeds to step 111.

At step 111, the actual trapped amount W of $SO_X$ is calculated from the detected value of the $SO_X$ sensor 13. Next, at step 112, the actual trapped amount $W_0$ of $SO_X$ before the time period TX1 is read. Next, at step 113, the increase $\Delta W(=W-W_0)$ in the actual trapped amount of the $SO_X$ during the time period TX1 is calculated.

Next, at step 114, the current assumed trapped amount WX of $SO_X$ calculated at the routine shown in FIG. 9 is read. Next, at step 115, the assumed trapped amount $WX_0$ of $SO_X$ before the time period TX1 is read. Next, at step 116, the increase $\Delta WX(=WX-WX_0)$ of the assumed trapped amount of $SO_X$ in the time period TX1 is calculated. Next, at step 117, W and WX are stored.

Next, at step 118, it is judged if the increase $\Delta W$ of the actual trapped amount of $SO_X$ has become larger than the increase $\Delta WX$ of the assumed trapped amount of $SO_X$ by a preset value KK or more, that is, $\Delta W - \Delta WX > KK$. When $\Delta W - \Delta WX \leq KK$, the processing cycle ends. As opposed to this, when $\Delta W - \Delta WX > KK$, the routine proceeds to step 119 where processing is performed for regeneration. Next, at step 120, it is judged if the regeneration processing has ended. When the regeneration processing has ended, the routine proceeds to step 121.

At step 121, the actual trapped amount W of $SO_X$ is calculated from the detected value of the $SO_X$ sensor 13. Next, at step 122, this actual trapped amount W is stored as $W_1$. Next, at step 123, the current assumed trapped amount WX of the $SO_X$ calculated in the routine shown in FIG. 9 is read. Next, at step 124, this assumed trapped amount WX is stored as $WX_1$. Next, at step 125, the check is started.

When the check is started, the routine proceeds from step 110 to step 126 where it is judged if the time period TX2 shown in FIGS. 12(A), (B) has elapsed. When the time period TX2 has not elapsed, the processing cycle is ended. As opposed to this, when the time period XT2 has elapsed, the routine proceeds to step 127 where the actual trapped amount W of $SO_X$ is calculated from the detected value of the $SO_X$ sensor 13. Next, at step 128, the increase $\Delta W_1(=W-W_1)$ in the actual trapped amount of the $SO_X$ during the time period TX2 is calculated.

Next, at step 129, the current assumed trapped amount WX of $SO_X$ calculated at the routine shown in FIG. 9 is read. Next, at step 130, the increase $\Delta WX_1(=WX-WX_1)$ of the assumed trapped amount of $SO_X$ in the time period TX2 is calculated. Next, at step 131, it is judged if the increase $\Delta W_1$ of the actual trapped amount of $SO_X$ has become larger than the increase $\Delta WX_1$ of the assumed trapped amount of $SO_X$ by a preset value KK or more, that is, $\Delta W_1-\Delta WX_1>KK$. When $\Delta W_1-\Delta WX_1>KK$, the routine proceeds to step 132 where it is judged if fuel or oil with a high sulfur concentration is being used. Next, at step 133, the check is ended.

LIST OF REFERENCE NOTATIONS

13 . . . $SO_X$ sensor
53 . . . metal compound piece for detection
55 . . . metal compound piece for reference
60 . . . metal compound for detection
63 . . . metal compound for reference

The invention claimed is:

1. A device for detection of the concentration of sulfur in fuel or oil, comprising:
   a metal or metal compound able to trap a sulfur component in exhaust gas arranged in a flow path of exhaust gas produced by combustion of fuel or oil, where a property of the metal or metal compound changing along with an increase in an amount of sulfur component trapped by the metal or metal compound is measured; and
   a controller configured to detect the amount of sulfur component trapped in the metal or metal compound from a measured property, to detect an actual cumulative value of an amount of $SO_X$ actually contained in the exhaust gas from a detected amount of sulfur component, to calculate an assumed cumulative value of an amount of $SO_X$, assumed to be included in the exhaust gas based on an operating state of the engine under the assumption that fuel or oil of a sulfur concentration assumed in advance is used, and to determine that fuel or oil of a sulfur concentration higher than the concentration of sulfur assumed in advance is being used when the actual cumulative value of the amount of $SO_X$ becomes larger than the assumed cumulative value of the amount of $SO_X$ by a predetermined value or more, wherein
   the actual cumulative value of the amount of $SO_X$ and the assumed cumulative value of the amount of $SO_X$ are cumulative values in a predetermined time period, and
   the predetermined time period starts advancing when the fuel is refilled or the oil is changed.

2. A device for detection of the concentration of sulfur in fuel or oil as claimed in claim 1, wherein said measured property is an electrical property represented by electrical resistance.

3. A device for detection of the concentration of sulfur in fuel or oil as claimed in claim 1, wherein said measured property is a thermal property represented by heat capacity and thermal conductivity.

4. A device for detection of the concentration of sulfur in fuel or oil as claimed in claim 1, wherein said metal or metal compound is an alkali metal, alkali earth metal, rare earth metal, precious metal, or compounds of these metals.

5. A device for detection of the concentration of sulfur in fuel or oil as claimed in claim 1, wherein said metal or metal compound includes Ba.

6. A device for detection of the concentration of sulfur in fuel or oil as claimed in claim 1, wherein said metal or metal compound includes Pd, Pt, or Rh.

7. A device for detection of the concentration of sulfur in fuel or oil, comprising:
   a metal or metal compound able to trap a sulfur component in exhaust gas arranged in a flow path of exhaust gas produced by combustion of fuel or oil, where a property of the metal or metal compound changing along with an increase in an amount of sulfur component trapped by the metal or metal compound is measured; and
   a controller configured to detect the amount of sulfur component trapped in the metal or metal compound from a measured property, to detect an actual cumulative value of an amount of $SO_X$ actually contained in the exhaust gas from a detected amount of sulfur component, to calculate an assumed cumulative value of an amount of $SO_X$, assumed to be included in the exhaust gas based on an operating state of the engine under the assumption that fuel or oil of a sulfur concentration assumed in advance is used, and to determine that fuel or oil of a sulfur concentration higher than the concentration of sulfur assumed in advance is being used when the actual cumulative value of the amount of $SO_X$ becomes larger than the assumed cumulative value of the amount of $SO_X$ by a predetermined value or more, wherein
   when said actual cumulative value of the amount of $SO_X$ becomes larger than said assumed cumulative value of the amount of $SO_X$ by the predetermined value or more, said metal or metal compound is regenerated and, when, in this regeneration processing, a rate of increase of said actual cumulative value of the amount of $SO_X$ is larger than a rate of increase of said assumed cumulative value of the amount of $SO_X$, it is first judged that fuel or oil of a sulfur concentration higher than a sulfur concentration assumed in advance is being used.

8. A device for detection of the concentration of sulfur in fuel or oil as claimed in claim 7, wherein:
   the actual cumulative value of the amount of $SO_X$ and the assumed cumulative value of the amount of $SO_X$ are cumulative values in a predetermined time period, and
   the predetermined time period starts advancing when the fuel is refilled or the oil is changed.

9. A device for detection of the concentration of sulfur in fuel or oil as claimed in claim 7, wherein said metal or metal compound includes Ba.

10. A device for detection of the concentration of sulfur in fuel or oil as claimed in claim 7, wherein said metal or metal compound includes Pd, Pt, or Rh.

11. A device for detection of the concentration of sulfur in fuel or oil, comprising:
   a metal compound able to trap a sulfur component in exhaust gas arranged in a flow path of exhaust gas produced by combustion of fuel or oil, where a property of the metal compound changing along with an increase in an amount of sulfur component trapped by the metal compound is measured; and
   a controller configured to detect the amount of sulfur component trapped in the metal compound from a measured property, to detect an actual cumulative value of an amount of $SO_X$ actually contained in the exhaust gas from a detected amount of sulfur component, to calculate an assumed cumulative value of an amount of $SO_X$, assumed to be included in the exhaust gas based on an operating state of the engine under the assumption that fuel or oil of a sulfur concentration assumed in advance is used, and to determine that fuel or oil of a sulfur concentration higher than the concentration of sulfur assumed in advance is being used when the actual cumulative value of the amount of $SO_X$ becomes larger than the assumed cumulative value of the amount of $SO_X$ by a predetermined value or more, wherein said metal compound changes from an oxide, carbonate, or nitrate to a sulfate along with an increase in the amount of sulfur component trapped by said metal compound.

12. A device for detection of the concentration of sulfur in fuel or oil as claimed in claim 11, wherein:

the actual cumulative value of the amount of $SO_X$ and the assumed cumulative value of the amount of $SO_X$ are cumulative values in a predetermined time period, and the predetermined time period starts advancing when the fuel is refilled or the oil is changed.

13. A device for detection of the concentration of sulfur in fuel or oil as claimed in claim 11, wherein when said actual cumulative value of the amount of $SO_X$ becomes larger than said assumed cumulative value of the amount of $SO_X$ by the predetermined value or more, said metal compound is regenerated and, when, in this regeneration processing, a rate of increase of said actual cumulative value of the amount of $SO_X$ is larger than a rate of increase of said assumed cumulative value of the amount of $SO_X$, it is first judged that fuel or oil of a sulfur concentration higher than a sulfur concentration assumed in advance is being used.

14. A device for detection of the concentration of sulfur in fuel or oil as claimed in claim 11, wherein said metal compound includes Ba.

15. A device for detection of the concentration of sulfur in fuel or oil as claimed in claim 11, wherein said metal compound includes Pd, Pt, or Rh.

16. A device for detection of the concentration of sulfur in fuel or oil, comprising:

a metal compound able to trap a sulfur component in exhaust gas arranged in a flow path of exhaust gas produced by combustion of fuel or oil, where a property of the metal compound changing along with an increase in an amount of sulfur component trapped by the metal compound is measured; and a controller configured to detect the amount of sulfur component trapped in the metal compound from a measured property, to detect an actual cumulative value of an amount of $SO_X$ actually contained in the exhaust as from a detected amount of sulfur component, to calculate an assumed cumulative value of an amount of $SO_X$, assumed to be included in the exhaust gas based on an operating state of the engine under the assumption that fuel or oil of a sulfur concentration assumed in advance is used, and to determine that fuel or oil of a sulfur concentration higher than the concentration of sulfur assumed in advance is being used when the actual cumulative value of the amount of $SO_X$ becomes larger than the assumed cumulative value of the amount of $SO_X$ by a predetermined value or more, wherein said metal compound is comprised of a metal compound for detection changing to a sulfate when trapping sulfur and a metal compound for reference comprised of a sulfate, and the sulfur component in the exhaust gas is detected from a difference of a measured property of the metal compound for detection and a measured property of the metal compound for reference.

17. A device for detection of the concentration of sulfur in fuel or oil as claimed in claim 16, wherein:

the actual cumulative value of the amount of $SO_X$ and the assumed cumulative value of the amount of $SO_X$ are cumulative values in a predetermined time period, and the predetermined time period starts advancing when the fuel is refilled or the oil is changed.

18. A device for detection of the concentration of sulfur in fuel or oil as claimed in claim 16, wherein when said actual cumulative value of the amount of $SO_X$ becomes larger than said assumed cumulative value of the amount of $SO_X$ by the predetermined value or more, said metal compound is regenerated and, when, in this regeneration processing, a rate of increase of said actual cumulative value of the amount of $SO_X$ is larger than a rate of increase of said assumed cumulative value of the amount of $SO_X$, it is first judged that fuel or oil of a sulfur concentration higher than a sulfur concentration assumed in advance is being used.

19. A device for detection of the concentration of sulfur in fuel or oil as claimed in claim 16, wherein said metal compound changes from an oxide, carbonate, or nitrate to a sulfate along with an increase in the amount of sulfur component trapped by said metal compound.

20. A device for detection of the concentration of sulfur in fuel or oil as claimed in claim 16, wherein said metal compound includes Ba.

21. A device for detection of the concentration of sulfur in fuel or oil as claimed in claim 16, wherein said metal compound includes Pd, Pt, or Rh.

\* \* \* \* \*